US012667324B2

(12) United States Patent
Miller et al.

(10) Patent No.: US 12,667,324 B2
(45) **Date of Patent: \*Jun. 30, 2026**

(54) DEFORMABLE IMAGE REGISTRATION PHANTOM COMPRISING A HOUSING, AN INNER CYLINDER, AN OUTER CYLINDER, A BALL AND SOCKET MOUNT, AND A TARGET

(71) Applicant: Modus Medical Devices Inc., London (CA)

(72) Inventors: David John Miller, London (CA); Michael James Cole, London (CA); Grant Richard Koenig, London (CA); Rocco Flores, London (CA)

(73) Assignee: Modus Medical Devices Inc., London (CA)

(\*) Notice: Subject to any disclaimer, the term of this patent is extended or adjusted under 35 U.S.C. 154(b) by 164 days.

This patent is subject to a terminal disclaimer.

(21) Appl. No.: 18/130,741

(22) Filed: Apr. 4, 2023

(65) Prior Publication Data

US 2023/0320689 A1     Oct. 12, 2023

Related U.S. Application Data

(60) Provisional application No. 63/326,964, filed on Apr. 4, 2022.

(51) Int. Cl.
*A61B 6/58*     (2024.01)
*A61N 5/10*     (2006.01)

(52) U.S. Cl.
CPC .............. *A61B 6/583* (2013.01); *A61B 6/584* (2013.01); *A61N 5/1075* (2013.01); *A61N 2005/1076* (2013.01)

(58) Field of Classification Search
CPC ......... A61B 6/582; A61B 6/583; A61B 6/584; A61B 6/585; A61N 5/1075; A61N 2005/1076
(Continued)

(56) References Cited

U.S. PATENT DOCUMENTS 5,793,835 A  \*  8/1998  Blanck ................... A61B 6/583
                                                              378/207
6,904,125 B2     6/2005  Van Dyk et al.
(Continued)

FOREIGN PATENT DOCUMENTS

WO          2014022480 A1     2/2014

OTHER PUBLICATIONS

Characterization of a new physical phantom for testing rigid and deformable image registration, Wu, et al., Radiation Oncology Physics, Wiley Online Library, Accepted Oct. 21, 2018, J Appl Clin Med Phys 2019; 20:1:145-153.

*Primary Examiner* — Allen C. Ho

(57)          ABSTRACT

A deformable image registration phantom, having a housing, an outer cylinder with a first diameter, a parallel eccentric inner cylinder with a second diameter smaller than the first diameter, a ball and socket mount, and a target. The target is mounted to the housing by way of the inner and outer cylinders and the ball and socket mount. The inner cylinder is rotatably mounted within the outer cylinder and the target is rotatably mounted, directly or indirectly, within the inner cylinder. The outer cylinder may be rotatably mounted within the housing and the ball and socket mount rotatably mounted within the inner cylinder. Alternatively, the outer cylinder may be rotatably mounted within the ball and socket mount and the ball and socket mount rotatably mounted within the housing.

17 Claims, 8 Drawing Sheets

(58) Field of Classification Search
USPC ............................................ 378/207, 18, 62
See application file for complete search history.

(56) References Cited

U.S. PATENT DOCUMENTS

| | | | | |
|---|---|---|---|---|
| 6,974,254 B2 * | 12/2005 | Paliwal | ................ | A61N 5/1048 |
| | | | | 378/65 |
| 7,510,325 B2 * | 3/2009 | Endo | ...................... | A61B 6/583 |
| | | | | 250/252.1 |
| 7,667,191 B2 * | 2/2010 | Serban | ................... | A61B 6/583 |
| | | | | 250/252.1 |
| 7,675,028 B2 * | 3/2010 | Breuer | ................... | A61B 6/583 |
| | | | | 250/252.1 |
| 7,699,522 B2 * | 4/2010 | Varchena | ............. | A61N 5/1049 |
| | | | | 378/207 |
| 8,039,790 B2 * | 10/2011 | Cho | ........................ | G01D 15/00 |
| | | | | 250/252.1 |
| 8,044,359 B2 * | 10/2011 | Simon | ................... | A61N 5/1071 |
| | | | | 378/207 |
| 8,189,889 B2 * | 5/2012 | Pearlstein | ............. | G06T 11/003 |
| | | | | 382/128 |
| 8,220,994 B2 * | 7/2012 | Heigl | ...................... | A61B 6/583 |
| | | | | 378/207 |
| 8,777,485 B2 * | 7/2014 | Holt | ........................ | A61B 6/583 |
| | | | | 378/207 |
| 8,891,849 B2 * | 11/2014 | Rohler | ................. | A61B 6/5252 |
| | | | | 382/132 |
| 8,895,912 B2 * | 11/2014 | Coolens | ................. | A61B 6/583 |
| | | | | 250/252.1 |
| 8,966,954 B2 * | 3/2015 | Ni | .......................... | G09B 23/30 |
| | | | | 73/1.86 |
| 9,259,192 B2 * | 2/2016 | Ishihara | ................. | A61B 6/583 |
| 9,398,889 B2 | 7/2016 | Kirby et al. | | |
| 9,480,861 B2 * | 11/2016 | Kapatoes | ............. | A61N 5/1071 |
| 9,606,242 B2 * | 3/2017 | Beaulieu | ................. | G01T 1/023 |
| 9,625,584 B1 * | 4/2017 | Cox | ........................ | A61B 6/583 |
| 9,681,851 B2 * | 6/2017 | Rohler | ................... | A61B 6/482 |
| 9,865,180 B2 * | 1/2018 | Saloux | ................... | A61B 8/587 |
| 9,872,658 B2 * | 1/2018 | Yamada | ................ | A61B 6/583 |
| 9,888,902 B2 * | 2/2018 | Ueki | ...................... | A61B 6/583 |
| 9,924,920 B2 * | 3/2018 | Gay | ........................ | A61B 6/583 |
| 10,022,104 B2 * | 7/2018 | Sell | ...................... | A61N 5/1075 |
| 10,028,720 B2 * | 7/2018 | Lin | ........................ | A61B 6/032 |
| 10,092,257 B2 * | 10/2018 | Wang | ..................... | A61B 6/583 |
| 10,180,483 B2 * | 1/2019 | Holdsworth | .......... | A61B 6/583 |
| 10,180,484 B2 * | 1/2019 | Barberi | ................. | G01R 33/58 |
| 10,448,918 B2 * | 10/2019 | Broggio | ................ | A61B 6/583 |
| 10,449,392 B2 * | 10/2019 | Suh | ...................... | A61N 5/1075 |
| 10,569,105 B2 * | 2/2020 | Kilby | ................... | A61N 5/1065 |
| 10,607,099 B2 * | 3/2020 | Cai | .......................... | G06T 7/66 |
| 10,660,600 B2 * | 5/2020 | Avila | ................... | A61B 6/583 |
| 10,667,780 B2 * | 6/2020 | Wu | ........................ | A61B 6/583 |
| 10,838,090 B1 * | 11/2020 | Holzmann | ............ | A61B 6/583 |
| 10,859,508 B2 | 12/2020 | Wu et al. | | |
| 10,939,891 B2 * | 3/2021 | Ruchala | ................. | A61B 6/583 |
| 10,977,839 B2 * | 4/2021 | Aichert | ................ | A61B 6/584 |
| 11,090,022 B2 * | 8/2021 | Zhao | ................... | A61B 6/5264 |
| 11,110,301 B2 * | 9/2021 | Yang | ................... | A61N 5/1081 |
| 11,246,559 B2 * | 2/2022 | Bornefalk | ............. | A61B 6/482 |
| 11,315,440 B2 * | 4/2022 | Yu | ......................... | A61B 6/583 |
| 11,369,806 B2 * | 6/2022 | Laurence, Jr. | ....... | A61N 5/1081 |
| 11,457,883 B1 * | 10/2022 | Hartley | ................. | A61B 6/584 |
| 11,540,767 B2 | 1/2023 | Gullotti et al. | | |
| 11,619,651 B2 * | 4/2023 | Barberi | ................. | A61B 8/587 |
| | | | | 324/76.11 |
| 12,089,982 B2 * | 9/2024 | Stringer, III | .......... | A61B 6/583 |
| 12,097,385 B2 * | 9/2024 | Kang | ................. | A61N 5/1075 |
| 12,121,380 B2 * | 10/2024 | Kojima | ................. | A61B 6/032 |
| 12,144,671 B2 * | 11/2024 | Stamm | ................... | A61B 6/583 |
| 12,146,934 B2 * | 11/2024 | Miller | ................... | G01T 1/023 |
| 12,427,342 B2 * | 9/2025 | Alexander | ........... | A61N 5/1075 |
| 12,471,876 B2 * | 11/2025 | Miller | ................... | A61B 6/584 |
| 12,514,530 B2 * | 1/2026 | Datta | ..................... | A61B 6/583 |
| 12,599,783 B2 * | 4/2026 | Freedman | ............ | A61N 5/1075 |

* cited by examiner

FIG. 2          FIG. 3

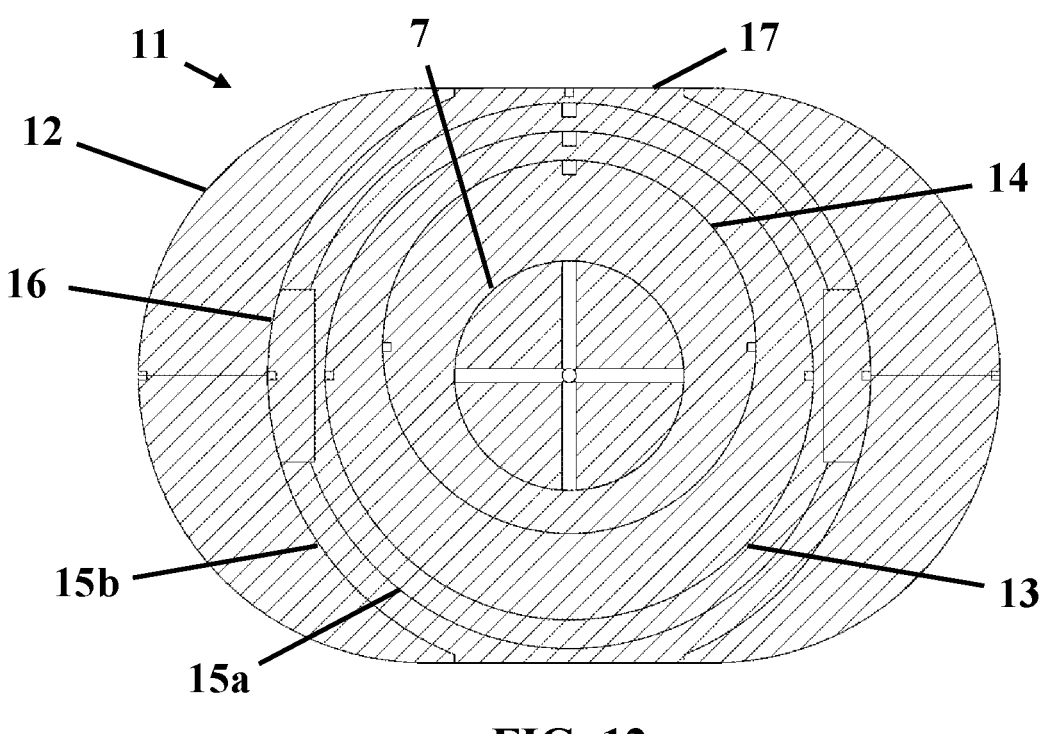
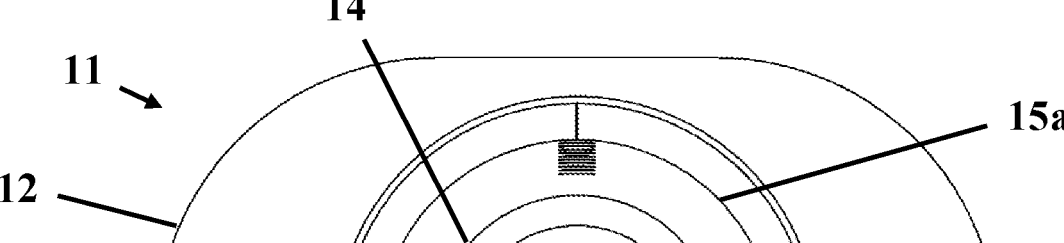
FIG. 12
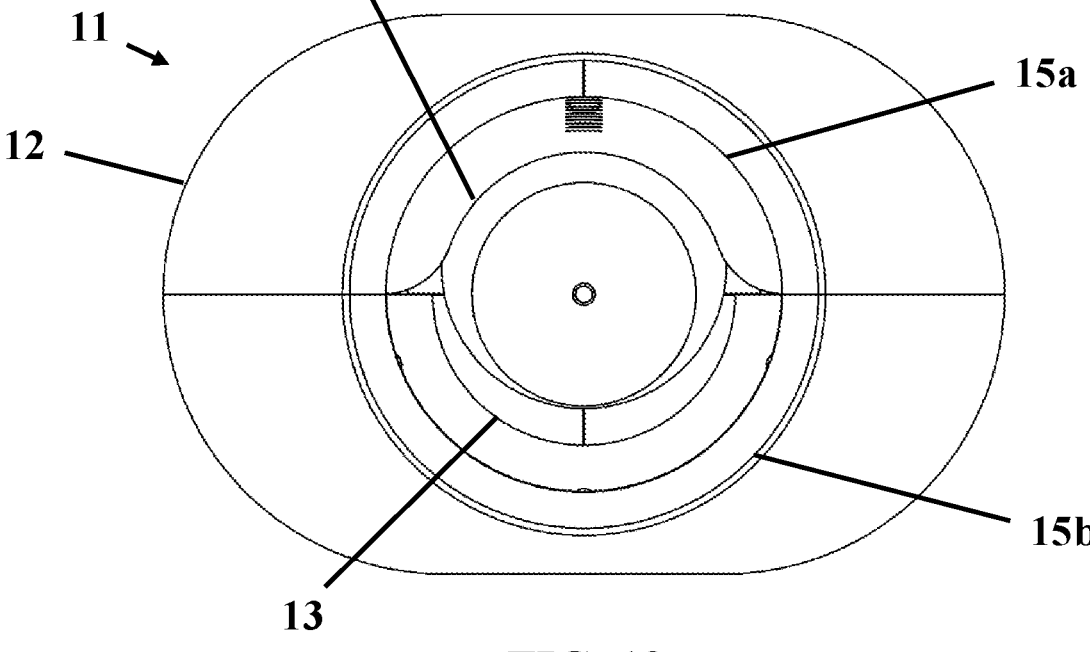
FIG. 13

DEFORMABLE IMAGE REGISTRATION PHANTOM COMPRISING A HOUSING, AN INNER CYLINDER, AN OUTER CYLINDER, A BALL AND SOCKET MOUNT, AND A TARGET

FIELD OF THE INVENTION

The present invention relates to an imaging quality assurance (QA) phantom apparatus and, in particular, to an adjustable deformable image registration phantom for on-table adaptive radiotherapy including dosimetry and dose accumulation.

BACKGROUND

Radiation treatment patients exhibit movement and deformation in many degrees of freedom, due to processes including weight loss, tumour shrinkage, inflammation, motion due to respiration, or simply lying in a slightly different position between treatment sessions. This presents challenges for radiation treatment in delivering the radiation dose to the target while minimizing the damage to surrounding healthy tissue or organs at risk.

Deformable image registration (DIR) is the process of finding correspondence between images that are not linked by simple translational shifts or rotations. This can be applied to many types of imaging, such as commutated tomography (CT) imaging or magnetic resonance imaging (MRI), and used in verification and adaptive treatment planning. The ability to model and adapt treatment plans for physiological changes, such as weight loss over the course of the treatment plan, will help clinicians reduce treatment margins, increase dose to the tumour, and decrease dose to healthy tissue. This permits more effective treatment of cancers associated with high mortality due to their proximity to other sensitive or moving organs, such as pancreatic, liver, and lung cancer.

The use of DIR in verifying and adapting treatment plans requires image quality assurance tools that are capable of producing quantified movements (both translational and rotational) and deformation. The present invention relates to the design of a DIR phantom capable of movement with six degrees of freedom and deformation, to verify the accuracy of the DIR process in treatment planning.

SUMMARY OF THE INVENTION

A deformable image registration phantom, according to the present invention, has a housing, an outer cylinder having a first diameter, a parallel eccentric inner cylinder having a second diameter smaller than the first diameter, a ball and socket mount, and a target. The target is mounted to the housing by way of the inner and outer cylinders and the ball and socket mount. The inner cylinder is rotatably mounted within the outer cylinder and the target is rotatably mounted, directly or indirectly, within the inner cylinder.

In another embodiment, the outer cylinder rotates about a first axis, the inner cylinder rotates about a second axis, and the second axis is parallel to the first axis and offset from the first axis by a first offset distance.

In another embodiment, the target is offset from the second axis by a second offset distance. The first and second offset distances may be equal in length.

In another embodiment, the target is a deformable target. The target may also comprise one or more radiation dose detectors.

In another embodiment, the outer cylinder is rotatably mounted within the housing, and the ball and socket mount is rotatably mounted within the inner cylinder and positioned with its centre of rotation offset from the second axis by the second offset distance.

In another embodiment, the outer cylinder is rotatably mounted within the ball and socket mount, and the ball and socket mount is rotatably mounted within the housing.

BRIEF DESCRIPTION OF THE DRAWINGS

In order that the invention may be more clearly understood, a preferred embodiment thereof will now be described in detail by way of example, with reference to the accompanying drawings, in which:

FIG. 2 is a front view of the phantom of FIG. 1.

FIG. 3 is a side view of the phantom of FIG. 1.

FIG. 12 is a front-sectional view of the phantom of FIG. 8, along the lines D-D as shown in FIG. 10.

FIG. 13 is a rear view of the phantom of FIG. 8.

DESCRIPTION OF THE INVENTION

Figure 1:
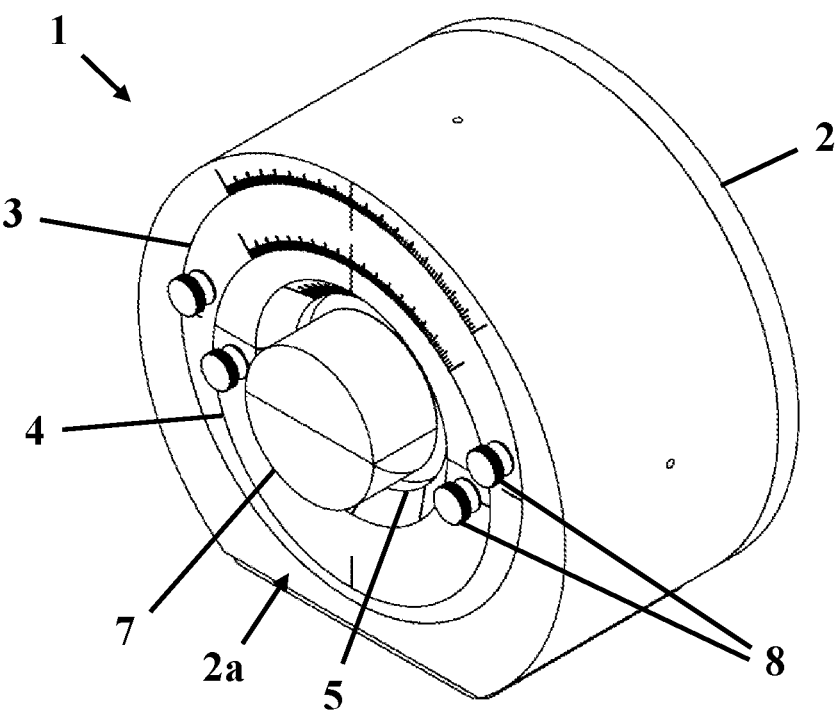
FIG. 1 is an isometric view of the deformable image registration phantom, according to the present invention.

The deformable image registration phantom, according to the present invention, permits controlled adjustment of the position of an imaging target in an imaging phantom with six degrees of freedom. A deformable imaging target may also be used to simulate any kind of movement or deformation of a target. The present invention may be used to test the accuracy of a piece of imaging equipment, such as a computerized tomography (CT) or magnetic resonance imaging (MRI) device, in tracking known movements and deformations of a target. This permits quality assurance of imaging equipment used for pre-treatment adjustments to radiation treatment plans. The target may also include one or more radiation dose detectors to permit confirmation of radiation dose delivery to the target, according to the adjusted treatment plan.

As shown in FIGS. 1-7, the phantom 1 has a housing 2, two parallel eccentric cylinders 3 and 4, a ball and socket mount 5, and a target 6. The housing 2 may have any desired shape or configuration, for example, a cylinder, a truncated cylinder or oval, or an anatomical shape, such as a torso, a skull, an abdomen, or a thorax. Preferably, the housing 2 is a truncated cylinder or oval to provide a flat, stable base for the phantom 1. The parallel eccentric cylinders comprise an outer cylinder 3 and an inner cylinder 4. The outer cylinder 3 is rotatably mounted within a complimentary shaped opening in the housing 2, so as to rotate about a first axis, and has a first diameter d₁. The inner cylinder 4 has a second diameter d₂ that is smaller than the first diameter d₁, and is rotatably mounted within a complimentary shaped opening in the outer cylinder 3, so as to rotate about a second axis. The second axis is parallel to the first axis and is also offset from the first axis by an offset distance D₁.

Figure 4:
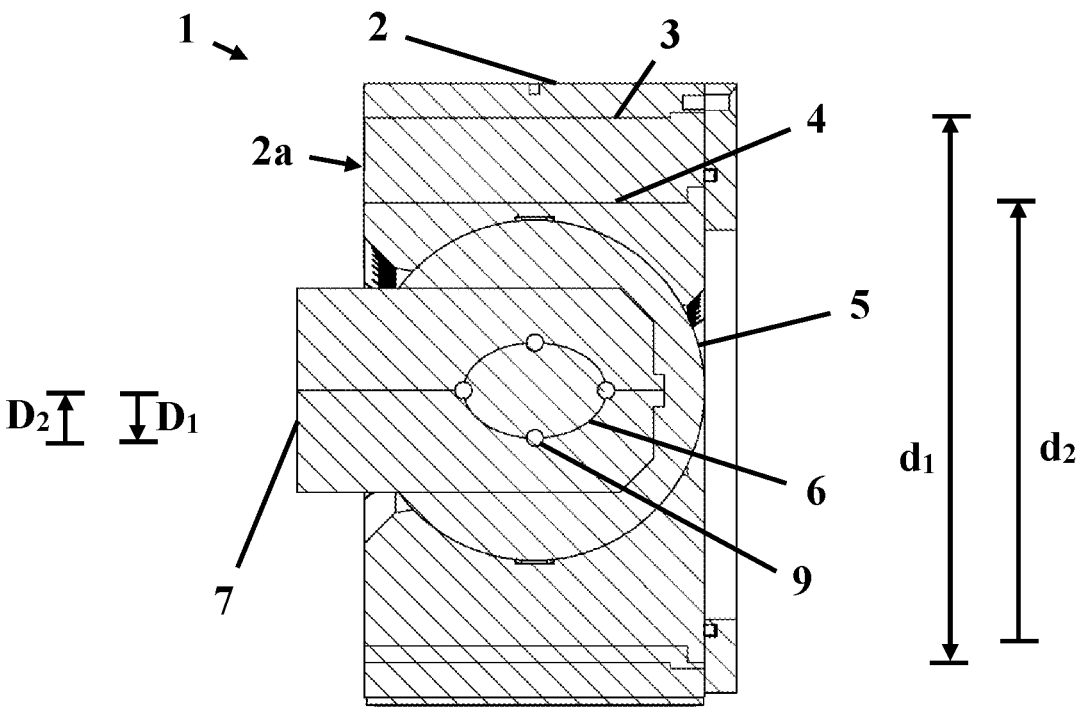
FIG. 4 is a side-sectional view of the phantom of FIG. 1, along the lines A-A as shown in FIG. 2.
Figure 5:
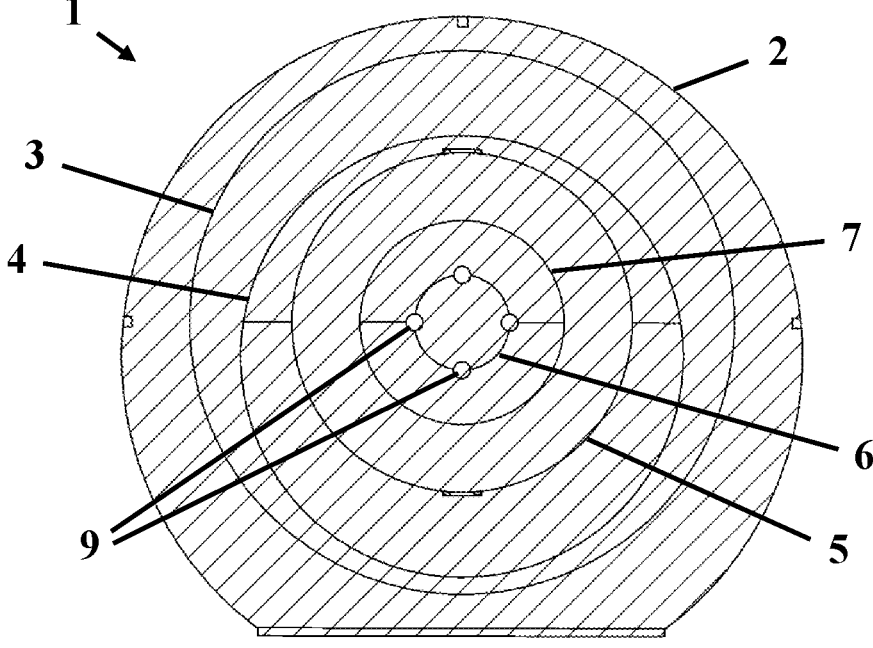
FIG. 5 is a front-sectional view of the phantom of FIG. 1, along the lines B-B as shown in FIG. 3.

As shown in FIGS. 2, 4, and 5, the ball and socket mount 5 for the target 6 is mounted within the inner cylinder 4. The ball and socket mount 5 is positioned with its centre of rotation offset from the second axis of the inner cylinder 4 by an offset distance D₂. As a result, the target 6 (within the ball and socket mount 5) moves relative to the housing 2 when either or both the inner cylinder 3 and outer cylinder 4 are rotated. The ball and socket mount 5 permits rotation of the target 6 about three axes (pitch, roll, and yaw). The target 6 may be any desirable configuration or type of target, but is preferably a cylindrical insert 7 containing a deformable imaging target 6, which slides into position at the centre of rotation of the ball and socket mount 5. This permits rotation of the target 6 along three axes (pitch, roll, and yaw) without displacement of the target 6 (i.e. movement along the x, y, or z axes). Alternatively, the target 6 may be offset from the centre of rotation of the ball and socket mount 2. A plurality of inserts 7 with variously sized targets 6 may be used and substituted for one another to simulate changes in overall size of the target 6, for example to simulate the reduction or growth in size of a tumour. The plurality of inserts 7 may also include targets 6 with various imaging properties. Inserts 7 may also be used, which include a plurality of targets 6 to simulate multiple radiation targets or organs at risk, or both. The term "target" will be used to refer generally to both radiation targets and organs at risk, but any particular target may be one or the other, as needed.

Figure 7:
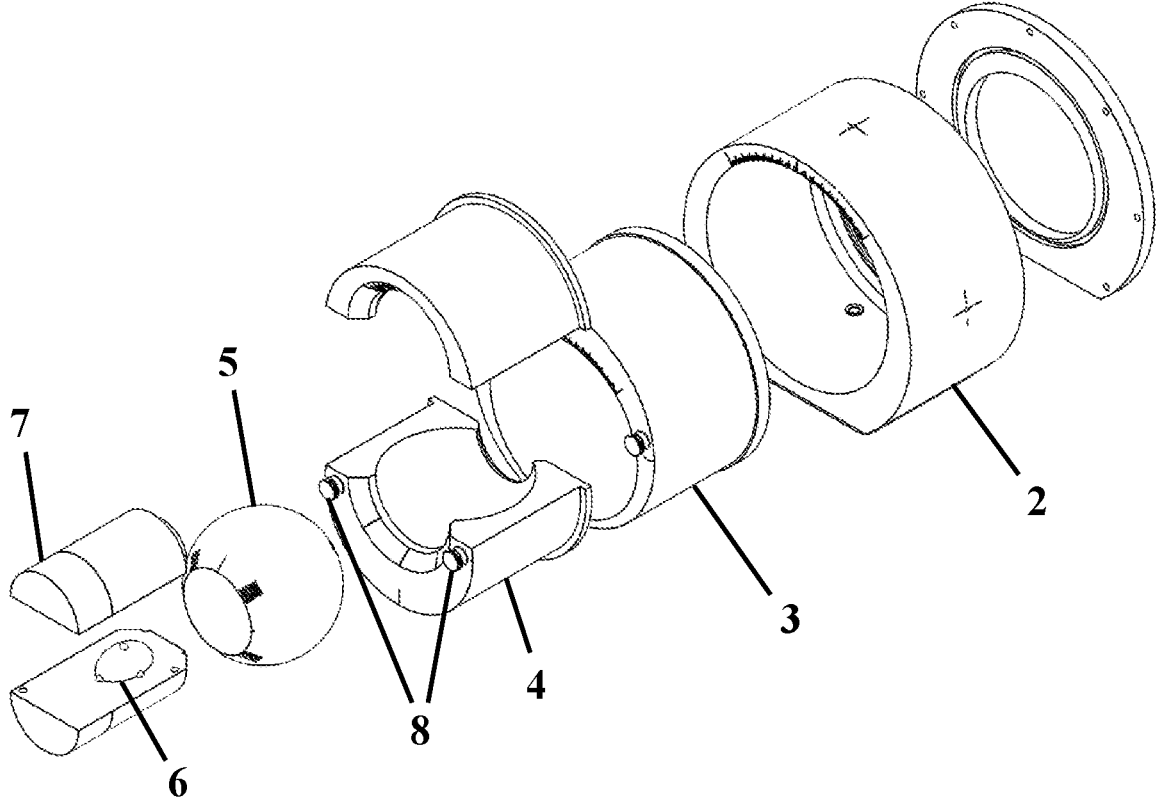
FIG. 7 is an exploded isometric view of the phantom of FIG. 1.

As shown in FIGS. 1, 2, and 7, the inner cylinder 4 has an opening through which the ball and socket mount 5 may be accessed for inserting or adjusting the position of the target 6. Preferably, the ball and socket mount 5 may be rotated unconstrained about the axis parallel to the second axis of the inner cylinder 4 (the roll axis). In configurations where an insert 7 protrudes from the ball and socket mount 5 so as to interfere with the free rotation of the ball and socket mount 5 about the two axes orthogonal to the second axis (the pitch and yaw axes), as shown in FIGS. 1 and 4, the rotation of the ball and socket mount 5 about these axes is constrained by the size of the insert 7 and the opening in the inner cylinder 4.

As shown in FIGS. 2, 4, and 5, the outer cylinder 3 and inner cylinder 4 may be rotated to a position where the offset distances D₁ and D₂ are oriented in opposite directions, such that the ball and socket mount 5 and target 6 are positioned at the centre of the phantom 1. This occurs when the offset distances D₁ and D₂ are equal in length. From that position, the target 6 may be displaced in the plane orthogonal to the first and second axes (i.e. on the x and y axes), by rotating either or both the outer cylinder 3 and the inner cylinder 4. Rotating the inner cylinder 4 within the outer cylinder 3 changes the distance between the centre of rotation of the ball and socket mount 5 and the first axis of the outer cylinder 3. Rotating the outer cylinder 3 within the housing 2 moves the centre of rotation of the ball and socket mount 5 along a circular path relative to the housing 2. By combining the rotation of the outer cylinder 3 and the inner cylinder 4, the centre of rotation of the ball and socket mount 5, and therefore the target 6, may be displaced to any location along the x and y axes within the area determined by the offset distances D₁ and D₂. Displacement in the z axis (the same axis as the first and second axes of the outer and inner cylinders 3 and 4) may be accomplished by sliding either the outer or inner cylinder 3 or 4, or where used, the insert 7, relative to other components of the phantom 1 in which they are mounted. Alternatively, the phantom 1 may be moved along the z axis on the imaging table in the imaging device.

Figure 6:
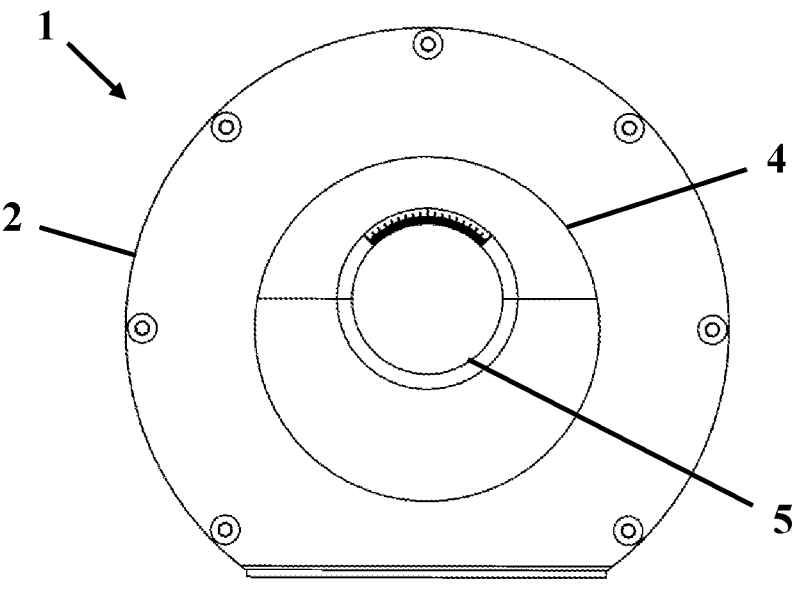
FIG. 6 is a rear view of the phantom of FIG. 1.
Figure 15:
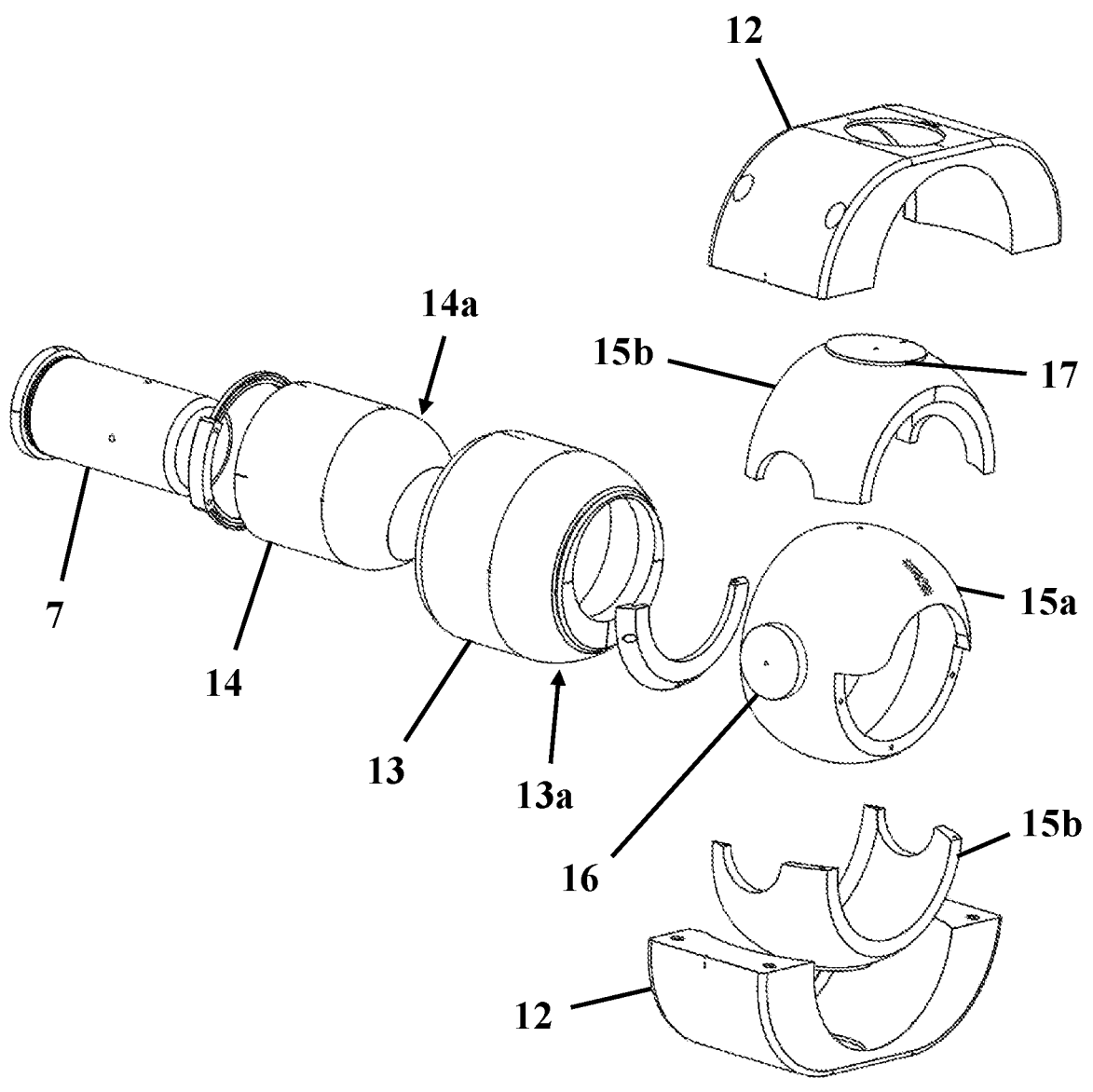
FIG. 15 is another exploded isometric view of the phantom of FIG. 8.

The movement of the outer and inner cylinders 3 and 4 may be manually controlled using control knobs 8 mounted on and accessible from the front 2a of the housing 2, as shown in FIGS. 2 and 3. The front 2a of the housing 2 may also have markings about the opening in which the outer cylinder 3 is mounted, to indicate the angle of rotation of the outer cylinder 3 relative to the housing 2. Similarly, the front 3a of the outer cylinder 3 may have visual markings about the opening in which the inner cylinder 4 is mounted, to indicate the angle of rotation of the inner cylinder 4 relative to the outer cylinder 3. Visual markers may also be provided on the rear of the phantom 1, such as on the inner cylinder 4, as shown in FIG. 6, or on the ball and socket mount 15, as shown in FIGS. 13, and 15. Alternatively, or in addition to visual markers, imaging structures, such as fiducials 9, may be added to one or more of the housing 2, outer cylinder 3, inner cylinder 4, ball and socket mount 5, insert 7, or target 6 to facilitate measurement of their relative position with the relevant imaging equipment and track adjustments more accurately than may be possible with visual observation and manual measurement by an imaging technician.

Although the phantom 1 has been described as configured with the ball and socket mount 5 located within the inner cylinder 4 (as shown in FIGS. 1-7), the phantom 1 may alternatively be configured the other way around, with the outer cylinder 4 located within the ball and socket mount 5 (as shown in FIGS. 8-15). This alternative configuration operates similarly to the configuration described above, but the relative positioning and mounting of the components are different. The target 6, or insert 7 containing the target 6, is located within or mounted in the inner cylinder 14, rather than the ball and socket mount 5, since the inner cylinder 14 is the innermost of these three components, in this configuration. In either configuration, the target 6 is mounted, directly or indirectly, within the inner cylinder 4 or 14.

Figure 11:
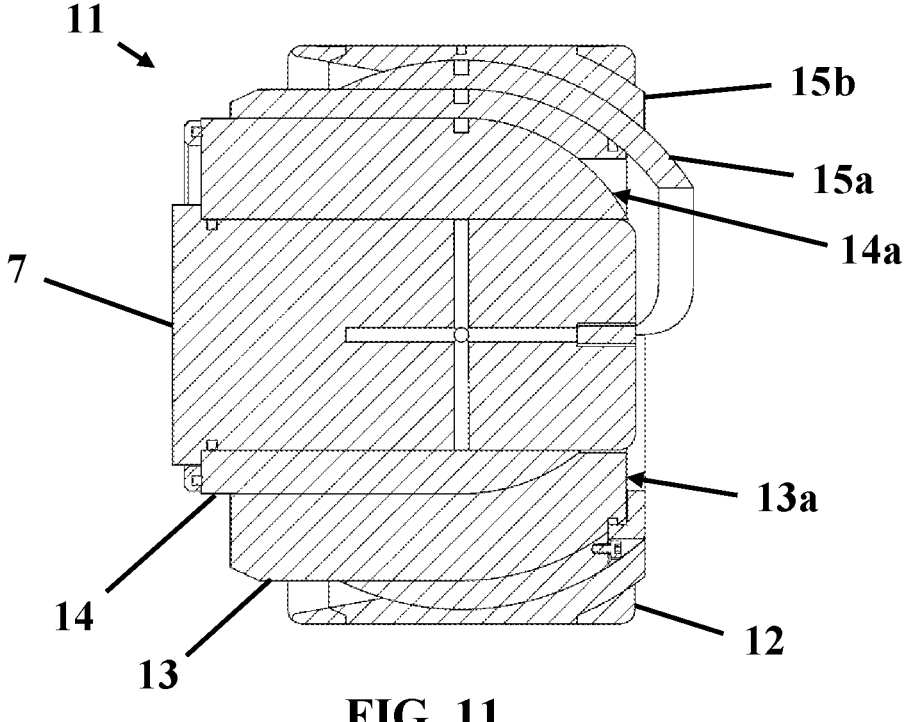
FIG. 11 is a side-sectional view of the phantom of FIG. 8, along the lines C-C as shown in FIG. 9.

The inner and outer cylinders 14 and 13 are both structurally and functionally similar to the configuration of the inner and outer cylinders 4 and 3, as described above. In both cases, they are parallel eccentric cylinders with first and second axes offset by an offset distance D₁. However, as shown in FIGS. 11, 14, and 15, the inner and outer cylinders 14 and 13 preferably have hemispherical rear ends 14a and 13a to fit and facilitate rotation within the ball and socket mount 5.

Figure 14:
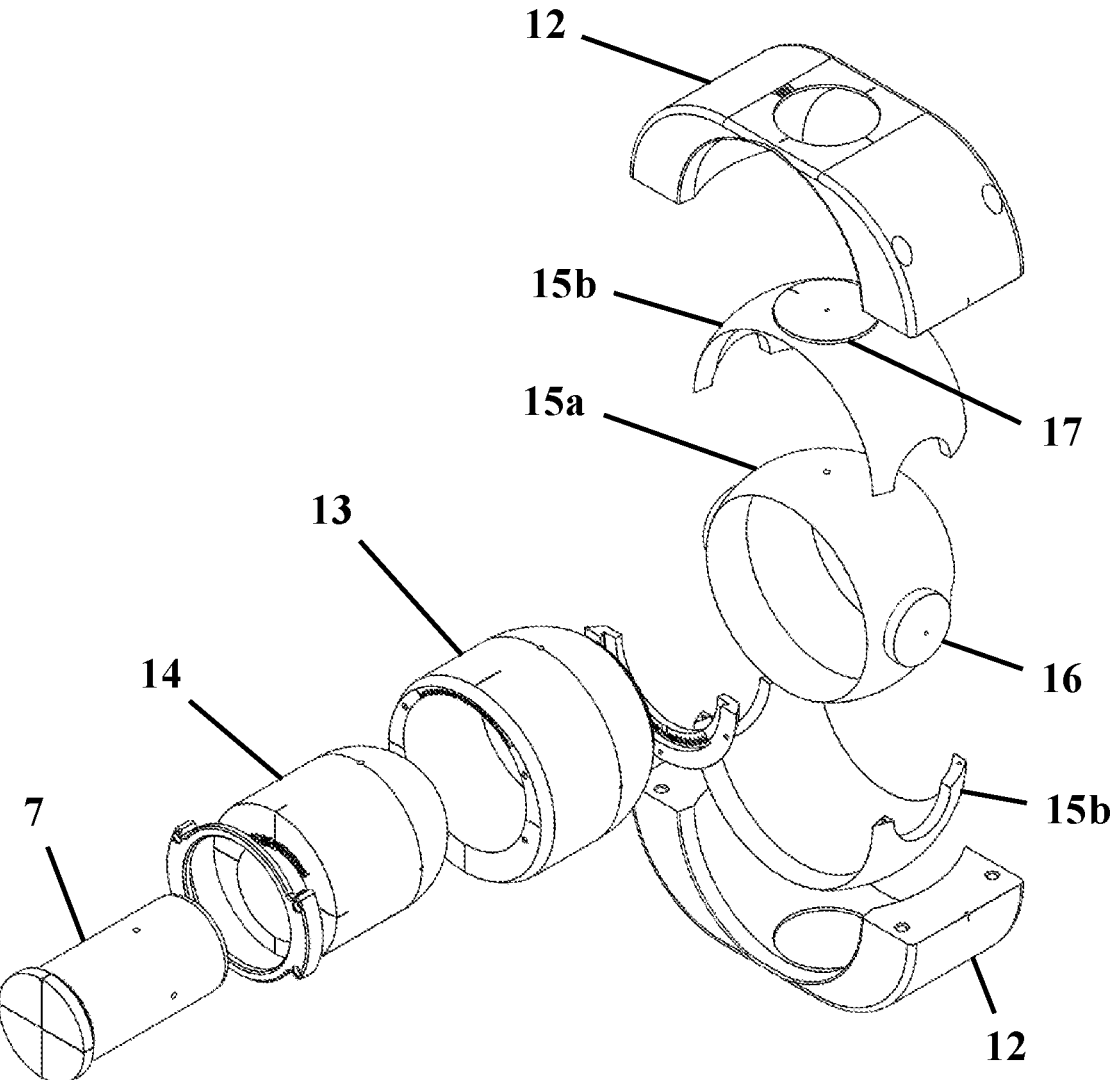
FIG. 14 is an exploded isometric view of the phantom of FIG. 8.

As shown in FIGS. 11, 12, 14, and 15, the ball and socket mount 15 is preferably a two-component ball and socket mount that operates like a gimbal mount, with an inner gimbal 15a and an outer gimbal 15b. The inner gimbal 15a has a third axis, about which it rotates, that is perpendicular to the first and second axes of the inner and outer cylinders 14 and 13. The outer gimbal 15b has a fourth axis, about which it rotates, that is perpendicular to the third axis of the inner gimbal 15a and also to the first and second axes of the inner and outer cylinders 14 and 13. As shown in FIG. 12, the inner gimbal 15a has a generally annular shape that fits within the outer gimbal 15b and accommodates the outer cylinder 13. In particular, the inner gimbal 15a has the shape of a spherical segment (or spherical frustum) with a hemispherical cylinder-shaped aperture through its centre. The outer gimbal 15b also has a generally annular shape to fit within the housing 12 and accommodate the inner gimbal 15a. Like the inner gimbal 15a, it has the shape of a spherical segment, but with a spherical segment-shaped aperture through its centre. Preferably, as shown in FIGS. 14 and 15, the inner gimbal 15a is formed in a single piece, while the outer gimbal 15b is formed in two pieces to facilitate ease of assembly.

Figure 8:
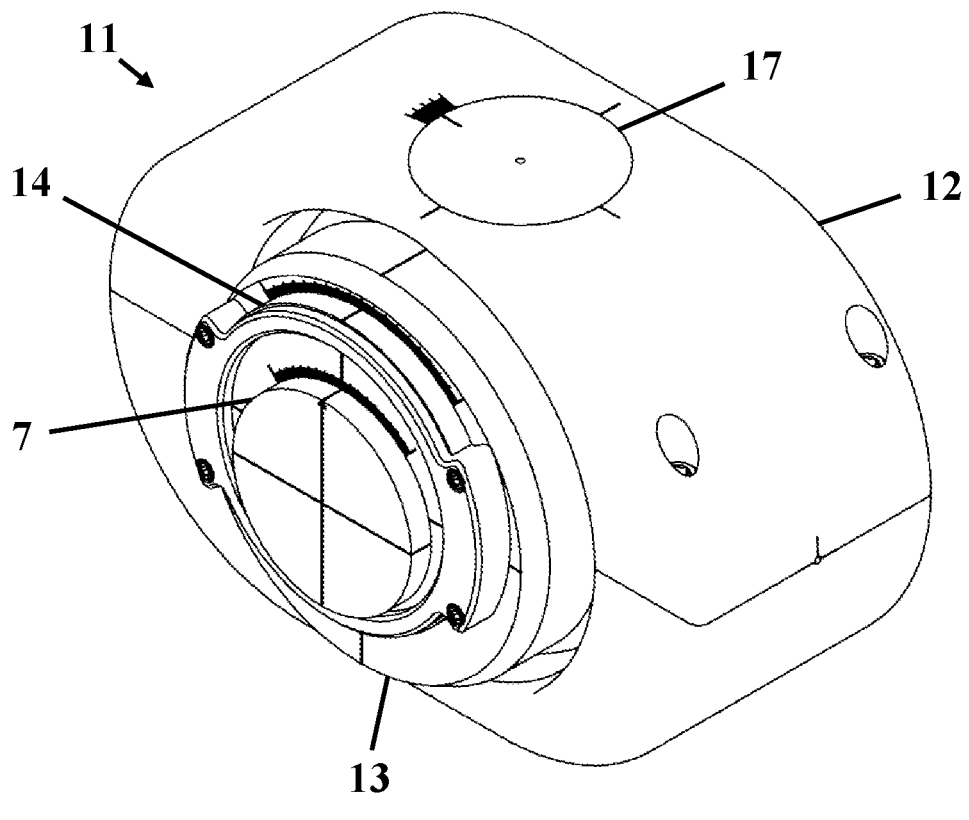
FIG. 8 is an isometric view of another embodiment of the deformable image registration phantom, according to the present invention.
Figure 9:
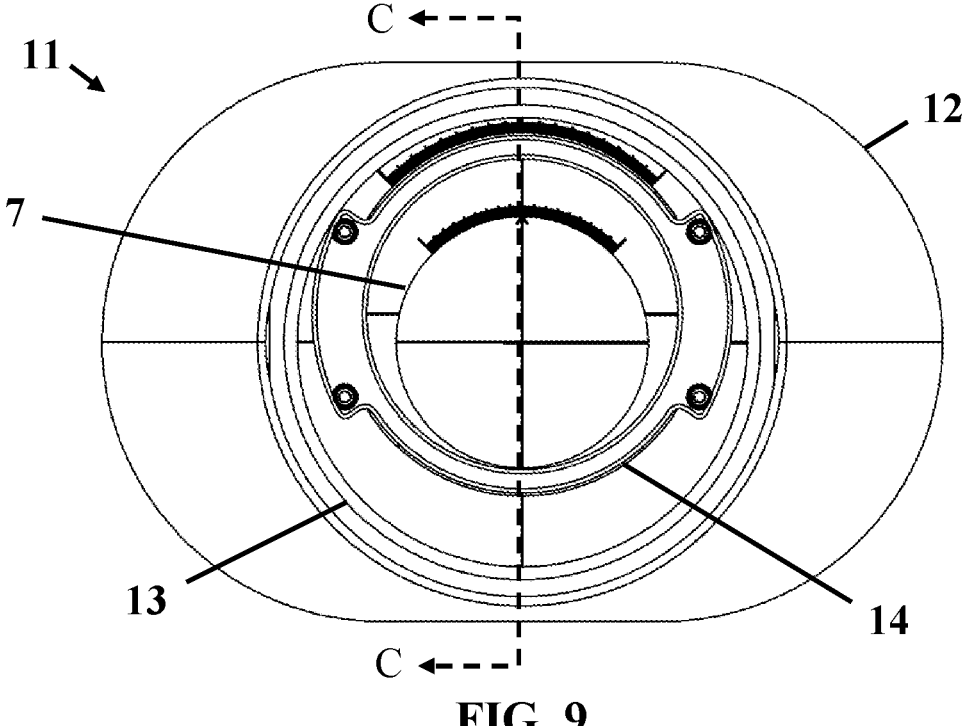
FIG. 9 is a front view of the phantom of FIG. 8.
Figure 10:
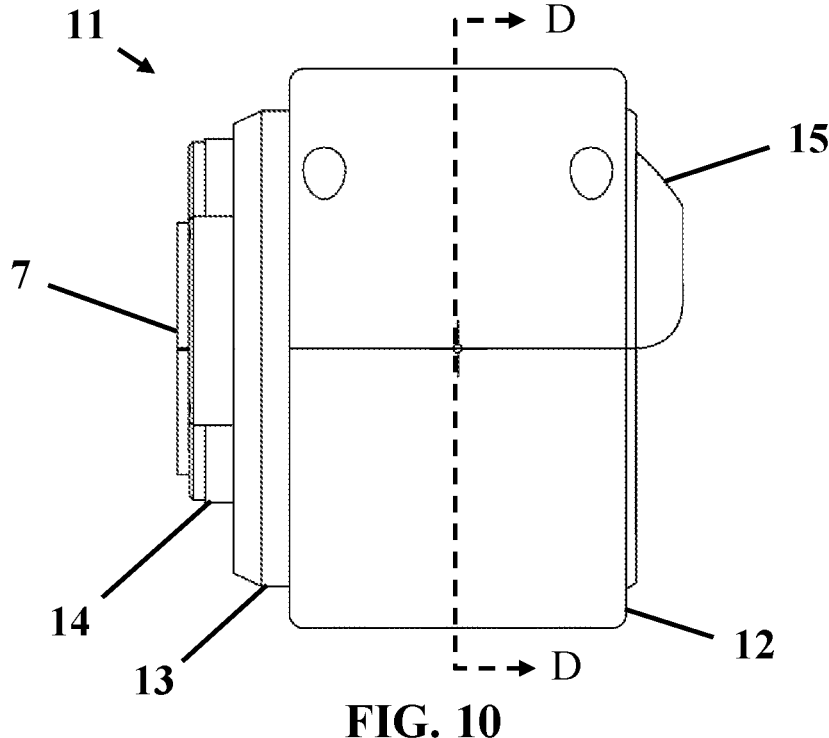
FIG. 10 is a side view of the phantom of FIG. 8.

As best illustrated in FIGS. 14 and 15, the inner gimbal 15a has posts 16 that extend outwardly from the inner gimbal 15a and engage with the outer gimbal 15b to restrict the movement of the inner gimbal 15a relative to the outer gimbal 15b to rotation about the third axis. Preferably, the posts 16 are no longer than the thickness of outer gimbal 15b, so as not to interfere with the movement of the outer gimbal 15b relative to the housing 12. Similarly, the outer gimbal 15b has posts 17 that extend outwardly from the outer gimbal 15b and engage with the housing 12 to restrict movement of the outer gimbal 15b relative to the housing 12 about the fourth axis. Preferably, the third and fourth axes are configured so that the rotation of the inner gimbal 15a adjusts the pitch, while the rotation of the outer gimbal 15b adjusts the yaw. Where the phantom 11 uses visual markers to indicate the relative position of the various components, the inner and outer cylinders 14 and 13 as well as the post 17 and the hemispherical rear end 13a of the outer cylinder 13 may marked with visual indicators to indicate the precise relative position of each component. In this case, the post 17 and the hemispherical rear end 13a are visible on the outside of the phantom 11, as shown in FIGS. 8, 13, and 15.

The phantom 1 may be configured for any desired imaging modality, such as X-ray, CT, PET, or MRI. Preferably, the phantom 1 and its components are made of a solid, rigid material for X-ray or CT imaging (kV or MV). Alternatively, the phantom 1, or one or more of its components, is configured for MRI or PET imaging and is made of a rigid (MRI invisible) material, containing one or more sealed reservoirs containing a fluid (MRI signal producing) material. Where the phantom 1 contains a sealed reservoir, it is preferably configured with a first and second volume portion, as described in U.S. Pat. Nos. 10,180,484 B2 or 10,310,048 B2 in the name of the present applicant. The first volume portion is the space defined by the side wall and end caps of the housing 2. The second volume portion is an expandable chamber or an expandable bladder attached to the housing 2 and in fluid communication with the first volume portion.

For MRI applications, the housing 2 is preferably made of acrylic, as it has closely matched susceptibility to human tissue, and the MRI signal producing material is an MRI contrast medium, such as aqueous solution with a close susceptibility match to human tissue. The aqueous solution is doped with one or more suitable T1 and T2 relaxivity modifiers, adjusted to give physiologically relevant T1 and T2 values with specific contrast between healthy tissue and tumors. Alternatively, the housing may be another human tissue equivalent susceptibility-matched plastic and the MRI contrast media may be an aqueous solution with added viscosity modifiers, mineral oil, silicone oil, vegetable oil, propylene glycol, or a gel that produces an MRI signal. Preferably, the relaxivity modifier is one or more of: copper (II) sulfate ($CuSO_4$), manganese (II) chloride ($MnCl_2$), gadolinium (III) chloride ($GdCl_3$), or other salts and chelates of paramagnetic metals that are soluble or freely dispersed in the MRI contrast media, superparamagnetic iron oxide nanoparticles (SPIONs), or micelles. Preferably, the phantom 1 is configured for multimodality applications, including two or more of: MRI, CT (MV or kV), and PET imaging.

In addition to multimodality imaging applications, the phantom 1 may be configured for use in dosimetry, gel dosimetry, deformable dose accumulation, deformable image registration (DIR), deformable image fusion, targeting, or gating applications. Preferably, in applications where dosimetry is desirable, the insert 7 contains one or more radiation dose detectors, such as ion chambers, diodes, OSLDs, scintillators, MOSFETs, diamond detectors, film diodes or chamber arrays, 3D gel or solid dosimeters. Preferably, the insert 7 contains a target 6 that is a gel imaging target or a gel-filled target for 3D imaging and dosimetry and is also deformable. Such deformable dosimeters can be formed by addition of radiation indicators, such as acrylamide and bis-acrylamide monomers, to a deformable hydrogel, where the radiation-induced polymerization can be determined by MRI, CT or optical methods. Other suitable indicators include radiochromic dyes, which may be added to a deformable hydrogel or to urethane or silicone rubber materials, where the radiation-induced color change can be determined by optical methods. Alternatively, the radiation-induced cross-linking of silicone or urethane rubbers, doped with appropriate additives, may be detected by MRI or CT imaging and used to measure the accumulated radiation dose. In the further alternative, an ion chamber or other radiation measurement device may be placed in a recess in the target 6, which may act as or receive an ion chamber holder.

The insert 7 may have the structure substantially similar to the deformable imaging phantom described in United States patent application publication US2020/0400716 A1, "Deformable Imaging Phantom for 4D Motion Tracking", by the present applicant. In such deformable applications, the insert 7 has a generally cylindrical shape, with a continuous side wall and two opposing end caps. The side wall and end caps define a sealed reservoir filled with an MRI contrast media and a deformable target 6. Preferably, the deformable target 6 is made of an open cell polyurethane foam, but other similar materials may be used, such as open cell poly(vinyl alcohol) foam, open cell silicone foam, closed cell foams, other foams, or other viscoelastic materials. Alternatively, continuous materials with viscoelastic properties and intrinsic MRI signal, such as urethane rubbers, silicone rubbers, or thermoplastic elastomers (such as styrene-ethylene-butylene-styrene co-polymer) may be used on viscoelastic hydrogels, based on natural or artificial gel forming polymers, such as gelatin, agarose, poly(vinyl alcohol), acrylamide-based polymers, or combinations thereof, with or without cross-linking agents, such as metal ion salts, aldehydes, amines, or acrylamides. Preferably, the deformable target 6 is in free contact with the MRI contrast media, which fills the sealed reservoir inside the insert 7 and the interstitial spaces in the deformable target 6, if any. Alternatively, the deformable target 6 may be enclosed in a thin-walled barrier, or coating, of deformable material, such as natural or artificial rubber, silicone, fluorosilicone rubber, or similar inert elastomers. Where a foam material is used, it is preferably impregnated with MR contrast media using a vacuum for air bubble removal to minimize MR and CT imaging artifacts in the target zone. The material is not limited to foam and could be a urethane rubber, thermoplastic elastomer (such as styrene-ethylene-butylene-styrene co-polymer), latex balloon, or hydrogel, with or without the addition of high-density, non-metallic, non-conductive powder for increased CT contrast. The different proton or electron densities of these regions results in different imaging properties. In FIG. 1, the target 6 is illustrated as a single off-centre ellipsoidal structure, but may have other positions and geometries, such as a spherical shape or the physiological shape of an organ or tumour.

Fiducial markers, or fiducials 9, may be positioned at any desired location within the phantom 1 for modeling verification, such as attached to the target 6 within the deformable insert 7, as shown in FIG. 1. The fiducials 9 may be additive or subtractive, positive or negative signal. Preferably, spherical fiducials 9 at least 3 mm in diameter are fixed to the target 6 and positioned on three orthogonal axes. The fiducials 9 provide verification for interpreting the position and motion of the target 6 on kV or MV CT imaging, for example. Where the fiducials 9 are intended to be used in MV CT applications, they must be of a sufficiently high-density material for visibility, such as an alumina or zirconia ceramic material. Alternatively, the fiducials 9 may be made of another high-density non-metallic material that is visible on MV. In a further alternative, fiducials 9 may not be necessary where the target 6, itself, has a density such that it is visible on kV and MV imaging. Fiducials may also be unnecessary for MR-only applications.

A motion assembly, such as a MR compatible motor system, may be connected to the insert 7 to drive the motion of the insert 7 relative to the housing 2 or to drive the deformation of a deformable target 6, or both. Preferably, the motion assembly is a MR compatible piezoelectric motor assembly, as described in U.S. Pat. No. 10,090,781 B2 in the name of the present applicant. Alternatively, other types of motion assemblies may be used, such as pneumatic or hydraulic drives.

The present invention has been described and illustrated with reference to an exemplary embodiment, however, it will be understood by those skilled in the art that various changes may be made and equivalents may be substituted for elements thereof without departing from the scope of the invention as set out in the following claims. Therefore, it is intended that the invention not be limited to the particular embodiments disclosed herein.

What is claimed is:

1. A deformable image registration phantom, comprising:
a housing,
an outer cylinder having a first diameter,
a parallel eccentric inner cylinder having a second diameter smaller than the first diameter,
a ball and socket mount, and
a target mounted to the housing by way of the parallel eccentric inner cylinder, the outer cylinder, and the ball and socket mount, wherein the parallel eccentric inner cylinder is rotatably mounted within the outer cylinder, and
wherein the target is rotatably mounted directly or indirectly within the parallel eccentric inner cylinder.

2. The deformable image registration phantom of claim 1, wherein the outer cylinder rotates about a first axis, the parallel eccentric inner cylinder rotates about a second axis, and the second axis is parallel to the first axis and offset from the first axis by a first offset distance.

3. The deformable image registration phantom of claim 2, wherein the target is offset from the second axis by a second offset distance.

4. The deformable image registration phantom of claim 3, wherein the first offset distance and the second offset distance are equal in length.

5. The deformable image registration phantom of claim 3, wherein the target is one or more targets, each independently configured to simulate a radiation target or an organ at risk.

6. The deformable image registration phantom of claim 3, wherein the target comprises one or more radiation dose detectors.

7. The deformable image registration phantom of claim 3, wherein the parallel eccentric inner cylinder, the outer cylinder, and the target are configures so that rotating the parallel eccentric inner cylinder or rotating both the parallel eccentric inner cylinder and the outer cylinder causes a displacement of the target in a plane orthogonal to the first axis and the second axis.

8. The deformable image registration phantom of claim 3, wherein the outer cylinder or the parallel eccentric inner cylinder is configured to slide along the first axis or the second axis, respectively, to displace the target along an axis parallel to the first axis and the second axis.

9. The deformable image registration phantom of claim 3, further comprising an insert, wherein the target is contained within the insert.

10. The deformable image registration phantom of claim 9, wherein the insert is configured to slide along an axis parallel to the first axis and the second axis to displace the target along the axis parallel to the first axis and the second axis.

11. The deformable image registration phantom of claim 3, further comprising a series of visual markings, wherein the series of visual markings are positioned on one or more of a front of the housing, a front of the parallel eccentric inner cylinder, a front of the outer cylinder, and the ball and socket mount to facilitate a measurement of relative positions of two or more of the housing, the parallel eccentric inner cylinder, the outer cylinder, and the ball and socket mount.

12. The deformable image registration phantom of claim 3, further comprising a plurality of imaging structures, wherein the plurality of imaging structures is positioned in one or more of the housing, the parallel eccentric inner cylinder, the outer cylinder, and the ball and socket mount to facilitate a measurement of relative positions of two or more of the housing, the parallel eccentric inner cylinder, the outer cylinder, and the ball and socket mount.

13. The deformable image registration phantom of claim 3, wherein the outer cylinder is rotatably mounted within the housing, and wherein the ball and socket mount is rotatably mounted within the parallel eccentric inner cylinder and positioned with its center of rotation offset from the second axis by the second offset distance.

14. The deformable image registration phantom of claim 13, wherein the ball and socket mount rotates about at least a third axis and a fourth axis, both perpendicular to the first axis and the second axis.

15. The deformable image registration phantom of claim 3, wherein the outer cylinder is rotatably mounted within the ball and socket mount, and wherein the ball and socket mount is rotatably mounted within the housing.

16. The deformable image registration phantom of claim 15, wherein the ball and socket mount comprises an inner gimbal and an outer gimbal.

17. The deformable image registration phantom of claim 16, wherein the inner gimbal rotates about a third axis perpendicular to the first axis and the second axis, and the outer gimbal rotates about a fourth axis perpendicular to the first axis, the second axis, and the third axis.

* * * * *